United States Patent [19]

Boudakian

[11] 4,310,671

[45] Jan. 12, 1982

[54] PROCESS FOR PRODUCING 2,6-DICHLORO-3-NITROPYRIDINE

[75] Inventor: Max M. Boudakian, Pittsford, N.Y.

[73] Assignee: Olin Corporation, New Haven, Conn.

[21] Appl. No.: 935,210

[22] Filed: Aug. 21, 1978

[51] Int. Cl.$^3$ .......................................... C07D 213/26
[52] U.S. Cl. .................................................. 546/304
[58] Field of Search ........................................ 546/304

[56] References Cited

PUBLICATIONS

Johnson et al., Journal Chem. Soc. (B) 1967 (II) pp. 1204–1210.

*Primary Examiner*—Alan L. Rotman
*Attorney, Agent, or Firm*—William A. Simons; Thomas P. O'Day

[57] ABSTRACT

A process for producing 2,6-dichloro-3-nitropyridine by reacting 2,6-dichloropyridine with nitric acid in the presence of about 10–65% strength by weight oleum.

10 Claims, No Drawings

PROCESS FOR PRODUCING 2,6-DICHLORO-3-NITROPYRIDINE

BACKGROUND OF THE INVENTION

1. Field of the Invention

This invention relates to a process for producing 2,6-dichloro-3-nitropyridine by an improved nitration process of 2,6-dichloropyridine.

2. Description of the Prior Art

It has been reported that 2,6-dichloro-3-nitropyridine has useful herbicidal properties. Furthermore, this compound is useful as a chemical intermediate for dyes, pharmaceutical and other agricultural applications.

It is known that 2,6-dichloropyridine could be nitrated with a mixture of $HNO_3$ and $H_2SO_4$ to give 2,6-dichloro-3-nitropyridine. See Johnson et al, J. Chem. Soc. (B), 1967, pp. 1204–1210 and U.S. Pat. No. 3,809,695, issued to Steinmetz et al on May 7, 1974. However, the nitration reactions disclosed by these prior art references employed relatively high molar ratios of $HNO_3$ to 2,6-dichloropyridines (i.e., both were over 10:1) to effect the nitration. Also, these inventions were accompanied by the evolution of hazardous brown nitrogen oxides from the reaction mixture. On large commercial scale operations, the employment of this relatively high molar ratio and evolution of hazardous fumes are both undesirable because of the low productivity associated with the high levels of $HNO_3$ needed and possible environment problems, respectively.

Accordingly, it would be beneficial if the conditions of this nitration reaction could be improved so that lower molar ratios of $HNO_3$ to 2,6-dichloropyridine could be employed and little or no evolution of nitrogen oxides occurred during the reaction.

BRIEF SUMMARY OF THE INVENTION

The present invention is, therefore, directed to a process for producing 2,6-dichloro-3-nitropyridine by reacting 2,6-dichloropyridine with nitric acid in the presence of about 10–65% strength oleum by weight. The employment of the oleum allows lower molar ratios of $HNO_3$ to 2,6-dichloropyridine (e.g., about 1.5:1) to be employed and little or no evolution of nitrogen oxides may occur.

DETAILED DESCRIPTION

The reaction of the present invention is believed to involve the in-situ formation of a 2,6-dichloropyridine:-$SO_3$ complex in the oleum. This reaction is illustrated as follows:

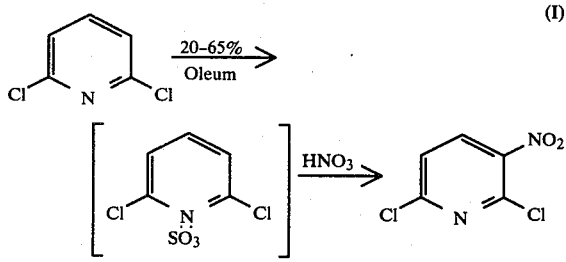

The reactants of the present invention may be drawn from any commercially available source. For example, 2,6-dichloropyridine may be obtained as the major by-product from processes which produce 2-chloropyridine. See U.S. Pat. Nos. 2,820,791, and 3,153,044, which issued to Shermer and Zaslowsky on Jan. 21, 1958, and Oct. 13, 1964, respectively. Preferably, the purity of the 2,6-dichloropyridine should be above about 98% by weight when pharmaceutical end uses are desired. But, when agricultural uses and the like are intended, the purity of the 2,6-dichloropyridine may be lower (e.g., above about 85% by weight). When the 2,6-dichloropyridine is obtained as a by-product from a process for producing 2-chloropyridine, the usual impurities associated with it may include the 2-chloropyridine, other isomeric dichloropyridines like 2,5-dichloropyridine, 2,3-dichloropyridine, 2,4-dichloropyridine and water.

Nitric acid ($HNO_3$) is also readily available from many sources. For example, suitable sources of this reactant include pure nitric acid (i.e., above about 95% by weight) or from a commercial "mixed acids" composed of $H_2SO_4/HNO_3$. In these mixed acids, suitable amounts of $HNO_3$ will normally include from about 10% to about 40% by weight $HNO_3$ with the balance being mostly $H_2SO_4$. Again, a high purity of this reactant is also preferred if the end use will be in pharmaceuticals. Thus, in that case, the purity of a suitable mixed acid will usually be composed of at least about 98% by weight $H_2SO_4$, $HNO_3$ and $H_2O$. Also, while this invention is primarily concerned with nitric acid being employed as the nitration agent, it may be possible in some instances to employ other conventional nitration agents like $KNO_3$ and $NaNO_3$.

The oleum employed in the present invention may be also obtained from any commercial source. The strength of the oleum should be from about 10% to about 65% by weight. The preferred range of oleum strength is from about 50% to about 65% by weight. The strength of oleum is designated as the weight percent of free sulfur trioxide ($SO_3$) in the acid solution. Thus, 10% oleum contains 10% by weight $SO_3$ and 90% by weight $H_2SO_4$. And, 65% oleum contains 65% by weight $SO_3$ and 35% by weight $H_2SO_4$.

In measuring the strength of the oleum for purposes of this invention, it is necessary to know the relative total amounts of $SO_3$ and $H_2SO_4$ in the reaction mixture. Thus, if a mixed acid system (i.e., mixture of $HNO_3/H_2SO_4$) is used as the source of nitric acid, this additional $H_2SO_4$ must be calculated into the total oleum strength.

These reactants may be combined by any conventional mode of addition including those methods shown in the following Examples. Specifically, it may be desirable to first add the 2,6-dichloropyridine and the oleum to the reactor, followed by slow addition of the nitric acid. Conversely, it is also possible to first add the nitric acid and oleum to the reactor, followed by the addition of the 2,6-dichloropyridine. Furthermore, the present invention also covers the in-situ formation of oleum e.g., liquid $SO_3$ is added to the reaction mixture, then followed by addition of 2,6-dichloropyridine. Also, the present invention includes the process where 2,6-dichloropyridine and nitric acid are combined at a relatively low temperature (e.g., from about 0° C. to 20° C.) and then oleum is added, followed by the increase in reaction temperature to a suitably high level.

The molar ratio of nitric acid to 2,6-dichloropyridine as reactants is not critical to the invention and any suitable ratio may be employed. Preferably, it may be suitable to employ a molar ratio of nitric acid to 2,6-dichloropyridine in the range from about 1:1 to about 20:1; more preferably, from about 1.5:1 to about 10:1; and most preferably, from about 2:1 to about 6:1. It is advantageous to employ excess HNO$_3$ because it will ensure complete reaction of the 2,6-dichloropyridine and possibly prevent substantial purification and product contamination problems. However, it should be noted suitable molar ratios for the process of this invention may be far less than the prior art methods discussed above which used only H$_2$SO$_4$, and not oleum. Specifically, those prior art methods used molar ratios of at least 10:1 nitric acid to 2,6-dichloropyridine, whereas the present invention may use more commercially advantageous ratios of about 1.5:1 to about 2:1.

The amount of oleum that may be used in the present process should preferably be enough to complex fully with the 2,6-dichloropyridine. Thus, it is preferred that at least about 1:1 molar ratio between the SO$_3$ and 2,6-dichloropyridine be employed. More preferably, this molar ratio of SO$_3$ to 2,6-dichloropyridine may be in the range of from about 2:1 to about 6:1, although larger ratios may also be desirable.

Any combination of reaction temperatures and times sufficient to convert a commercially acceptable amount of 2,6-dichloropyridine to 2,6-dichloro-3-nitropyridine may be employed. Usually, temperatures in the range of about 85° C. to about 150° C. may be employed. Times in the range from about 60 minutes to 600 minutes also may be used. It should be understood that the reaction conditions, other than the reactants and employment of oleum, are not critical to the present invention and one having ordinary skill in the art would be able to select the optimum reaction temperatures and times. Of course, the optimum reaction temperature and time depend on many factors, including equipment being employed, molar ratio of reactants, reaction pressure and the like.

Any suitable method for removing the desired product, 2,6-dichloro-3-nitropyridine may be utilized. One preferred method is to first add water (or vice-versa) to the reaction mixture after completion of the reaction to cause precipitation of the desired product. This precipitated product is then removed from the resulting solution by filtration. The filtrate containing the product is then water-washed to remove any occluded nitric and sulfuric acids. The resulting product can then be easily dried by any conventional means. It should be noted that the addition of water to the reaction mixture may convert any SO$_3$ in the oleum into H$_2$SO$_4$. Thus, this water quenching purification removes the SO$_3$ without the need for an additional separation step. Also, it should be appreciated that when the product will be used for pharmaceutical or other high-purity applications, further purification such as with conventional recrystallization techniques may be employed.

While this invention is primarily directed toward the nitration of 2,6-dichloropyridine in the presence of oleum, the inventive concept should be effective with other dichloropyridines such as 2,3-dichloropyridine; 2,4-dichloropyridine; 2,5-dichloropyridine; 3,4-dichloropyridine; and 3,5-dichloropyridine. Also, the present invention may be useful with corresponding dibromopyridines and difluoropyridines such as 2,6-difluoropyridine. But, it is believed that this oleum nitration technique is not readily useful for the nitration of monohalopyridines such as 2-chloropyridines.

The following examples and comparisons are given to further illustrate the present invention. All percentages and proportions are by weight unless otherwise explicitly indicated.

EXAMPLE 1

2,6-Dichloropyridine (0.20 mole; 29.6 grams; VPC assay: 99.9%; H$_2$O content, 0.24%) was added to 100 grams of 65% oleum (SO$_3$ content, 0.80 mole) at 0° C. To this slurry was added 84.0 grams of 30% nitric acid/68% sulfuric acid (HNO$_3$ content, 0.40 mole) over a 15 minute period (5° to 20° C.). The mixture was heated at 80°–142° C. over a 5.5 hour period. Virtually no brown fumes were evolved during the heat-up period. The additional H$_2$SO$_4$ in the mixed acid lowered the oleum strength to about 16% by weight.

The straw-colored nitration solution (20° C.) was then transferred to 800 grams water (0° C.) over a 20 minute period to precipitate 3-nitro-2,6-dichloropyridine. The filter cake was washed with water to remove occluded nitric and sulfuric acid. The pale yellow precipitate was air-dried, wt. 28.4 grams (m.p. 54.5°–60.5° C.) and had a % H$_2$O of 0.56% by weight and a VPC assay as follows:

|  | VPC | Moles |
| --- | --- | --- |
| 2-6-Dichloropyridine | 5.7% | 0.011 |
| 3-Nitro-2,6-Dichloropyridine | 93.3% | 0.137 |

The uncorrected yield of 3-nitro-2,6-dichloropyridine was 68.5%. Corrected for 94.5% conversion of 2,6-dichloropyridine, the adjusted yield is 72.5%.

Purification of crude 3-nitro-2,6-dichloropyridine (wt. 24.5 grams) can be effected by recrystallization from a 50% aqueous i-propylalcohol solution (156 grams) to give 21.0 grams of product, m.p. 61°–63° C. VPC assay: 97.2% 3-nitro-2,6-dichloropyridine.

EXAMPLE 2

The conditions of Example 1 were repeated, except that a more narrow temperature range (94°–112° C./6.0 hours instead of 80°–142° C./5.5 hours) were employed. Conversion of the 2,6-dichloropyridine was lowered as the following results before recrystallization indicate:

| % 2,6-Dichloropyridine Conversion | 75.4% |
| --- | --- |
| % 2,6-Dichloro-3-Nitropyridine Yield |  |
| Uncorrected | 55.7% |
| Corrected | 73.9% |

Again, virtually no brown fumes were evolved during the heat-up period.

EXAMPLE 3

2,6-Dichloropyridine (0.20 mole; 29.6 grams; VPC, 99.9%; H$_2$O, 0.24%) was added to 160 grams 20% oleum (SO$_3$ content, 0.40 mole) at 0° C. To this cream-colored solution was added 63 grams of 30% nitric acid/68% sulfuric acid (HNO$_3$ content, 0.30 mole) over a 20 minute period (17.5°–28° C.). The mixture was heated at 88°–144° C. (2 hours). Virtually no brown fumes were evolved during the heat-up period. Again, the additional H$_2$SO$_4$ from the mixed acid lowered the oleum strength to about 16%.

The straw-colored solution was processed by transfer to water (0° C.), the 2,6-dichloro-3-nitropyridine was filtered and washed free of occluded acid and air-dried, wt. 28.7 grams. Assay: 2,6-dichloropyridine (22.2%—VPC, 0.043 mole; 78.5% conversion), 2,6-dichloro-3-nitropyridine (77.5%—VPC; 0.115 mole; 57.5% uncorrected yield; 73.2% corrected yield).

EXAMPLE 4

The conditions of Example 3 were repeated and the following results were obtained with the following reactant ratios:

| 2,6-Dichloropyridine | 0.20 mole |
|---|---|
| SO$_3$ in Oleum | 0.30 mole |
| Nitric Acid | 0.22 mole |

Conversion of 2,6-dichloropyridine was 59.7%; Yield of 2,6-dichloro-3-nitropyridine was 46% (uncorrected) and 77% (corrected). Again, virtually no brown fumes were evolved.

EXAMPLE 5

2,6-Dichloropyridine (0.20 mole; 29.6 grams; VPC, 99.8%; H$_2$O, 0.06%) was added to 100 grams of 65% oleum (SO$_3$ content; 0.80 mole) at 0° C. To this mixture was added 19.4 grams of white fuming nitric acid (97.2% assay; 0.30 mole) over a 20 minute period. The nitration mixture was heated at 68° to 134° C. (5.5 hours). No brown fumes were evolved during this heating period.

The straw-colored solution was then transferred to 800 grams of water (0° C.) to precipitate 3-nitro-2,6-dichloropyridine. The filter cake was washed with water to remove occluded nitric acid and sulfuric acid. The precipitate was air-dried wt. 29.9 grams; m.p 51°-55° C.; % H$_2$O 0.80%.

Assay: 2,6-dichloropyridine (22.6%—VPC; 0.045 mole; 77.5% conversion); 2,6-dichloro-3-nitropyridine (%75.4—VPC; 0.116 mole; 58.0% uncorrected yield; 74.8% corrected yield).

EXAMPLE 6

2,6-Dichloropyridine (0.20 mole; 29.6 grams; VPC, 99.8%; H$_2$O, 0.06%) was added to 160 grams 20% oleum (SO$_3$ content; 0.40 mole) at 0° C. To this mixture was added 19.4 grams of white fuming nitric acid (97.2% assay; 0.30 mole) over a 5 minute period (8° to 15° C.). The nitration mixture was heated at about 70° to about 130° C. (6 hours). No brown fumes were evolved during this heating period.

The straw-colored solution was processed by transfer to 800 grams water (0° C.), 2,6-dichloro-3-nitropyridine was filtered and washed free of occluded acid and air-dried, wt. 26.7 grams; m.p. 59°-60° C.; % H$_2$O 0.83%. Assay: 2,6-dichloropyridine (15.6%—VPC; 0.28 mole; 86% conversion); 2,6-dichloro-3-nitropyridine (%84.3—VPC; 0.116 mole; 58.0% uncorrected yield; 67.4% corrected yield).

COMPARISON I 2,6-Dichloropyridine (0.20 mole; 29.6 grams; VPC assay, 99.9%; H$_2$O content, 0.24%) was added to 548.0 grams of 30% nitric acid/68% sulfuric acid (HNO$_3$ content: 2.6 moles) and the straw-colored solution heated to reflux (108° C.) for 2.2 hours. Throughout this period, copious evolution of brown nitrogen oxides were continuously evolved.

The nitration solution (20° C.) was then transferred to 800 grams H$_2$O (0° C.) over a 15 minute period to precipitate 3-nitro-2,6-dichloropyridine. The filter cake was washed with water to remove occluded nitric and sulfuric acids. The yellow precipitate was air dried, wt. 30.0 grams (m.p. 61°-64° C.) and had a %H$_2$O of 1.05% and VPC assay as follows:

| | VPC | Moles |
|---|---|---|
| 2,6-Dichloropyridine | 2.9% | 0.006 |
| 3-Nitro-2,6-Dichloropyridine | 97.1% | 0.149 |

The uncorrected yield of 3-nitro-2,6-dichloropyridine was 74.5%. Corrected for 97.0% 2,6-dichloropyridine conversion, the adjusted yield is 76.8%.

COMPARISON II 2,6-Dichloropyridine (0.20 mole; 29.6 gms.; VPC assay, 99.8%; H$_2$O content, 0.06%) was added to 84.0 gms. of 30% nitric acid/68% sulfuric acid (HNO$_3$ content; 0.40 mole) and the straw-colored solution heated at 84°-142° C. over a 5.5 hour period. Throughout this heating cycle, copious evolution of brown nitrogen oxide fumes were continuously evolved.

The nitration solution (10° C.) was then added to 800 ml. H$_2$O (0° C.) to precipitate organics. The filter cake was washed with 500 ml. to remove occluded nitric and sulfuric acids. The white precipitate was air dried, wt. 23.0 gms., m.p. 84°-86° C. and had %H$_2$O of 14.5% and VPC assay as follows:

| | VPC |
|---|---|
| 2,6-Dichloropyridine | 99.7% |
| 3-Nitro-2,6-Dichloropyridine | 0.3% |

This comparison shows that low molar ratios of HNO$_3$:2,6-dichloropyridine (in the absence of oleum) will be unable to sufficiently cause conversion to 2,6-dichloro-3-nitropyridine.

What is claimed is:

1. A process for producing 2,6-dichloro-3-nitropyridine comprising:
    reacting 2,6-dichloropyridine with nitric acid in the presence of about 10-65% strength by weight oleum to produce a reaction mixture comprising 2,6-dichloro-3-nitropyridine.
2. The process of claim 1 wherein the molar ratio of said nitric acid to said 2,6-dichloropyridine is in the range from about 1:1 to about 20:1.
3. The process of claim 1 wherein the molar ratio of the SO$_3$ in said oleum to said 2,6-dichloropyridine is at least about 1:1.
4. The process of claim 1 wherein the reaction temperature is in the range from about 85° C. to about 150° C.
5. The process of claim 1 wherein the source of said nitric acid is a mixed acid comprising H$_2$SO$_4$ and HNO$_3$.
6. The process of claim 1 wherein said strength of said oleum is in the range of about 50% by weight to about 65% by weight.
7. A process for producing 2,6-dichloro-3-nitropyridine comprising:
    reacting 2,6-dichloropyridine with nitric acid in the presence of about 10-65% strength by weight oleum to process a reaction mixture comprising 2,6-dichloro-3-nitropyridine, wherein the molar ratio of said nitric acid to said 2,6-dichloropyridine is in the range from about 1.5:1 to about 10:1, the molar ratio of the SO$_3$ in said oleum to said 2,6-dichloropyridine is in the range from about 2:1 to about 6:1, and the reaction temperature is in the range of about 85° C. to about 150° C.

8. The process of claim 7 wherein the source of said nitric acid is a mixed acid comprising H$_2$SO$_4$ and HNO$_3$.

9. The process of claim 8 wherein said molar ratio of said nitric acid to said 2,6-dichloropyridine is in the range from about 2:1 to about 6:1.

10. The process of claim 9 wherein said strength of said oleum is in the range of about 50% by weight to about 65% by weight.

* * * * *